United States Patent [19]

Chibata et al.

[11] 4,309,362

[45] Jan. 5, 1982

[54] PROCESS FOR THE OPTICAL RESOLUTION OF DL-P-HYDROXY-PHENYLGLYCINE

[75] Inventors: Ichiro Chibata, Suita; Shigeki Yamada, Toyonaka; Chikara Hongo, Osaka, all of Japan

[73] Assignee: Tanabe Seiyaku Co., Ltd., Osaka, Japan

[21] Appl. No.: 885,804

[22] Filed: Mar. 13, 1978

Related U.S. Application Data

[63] Continuation of Ser. No. 756,079, Jan. 3, 1977, abandoned.

[30] Foreign Application Priority Data

Jan. 13, 1976 [JP] Japan ................................. 51/3344
Jan. 13, 1976 [JP] Japan ................................. 51/3345

[51] Int. Cl.$^3$ .......................................... C07C 145/00
[52] U.S. Cl. ............................................. 260/501.12
[58] Field of Search .................................. 260/501.12

[56] References Cited

U.S. PATENT DOCUMENTS 3,994,962  11/1976  Shirai et al. .................. 260/501.12

OTHER PUBLICATIONS

Secor, Chemical Reviews 63, 297–308 (1963).

*Primary Examiner*—Alan Siegel
*Attorney, Agent, or Firm*—Bierman & Bierman

[57] ABSTRACT

Seed crystals of an optically active enantiomer of any one of p-hydroxyphenylglycine benzenesulfonate, p-hydroxyphenylglycine p-ethylbenzenesulfonate, p-hydroxyphenylglycine o-toluenesulfonate or p-hydroxyphenylglycine sulfosalicylate are added to a supersaturated solution of the racemic modification of the corresponding p-hydroxyphenylglycine salt. Crystallization of the optically active enantiomer results. Then, the crystals are recovered. Alternatively, crystals of the optically active enantiomer may be added to a hot solution of the racemic modification of the corresponding p-hydroxyphenylglycine salt to produce a supersaturated solution thereof. The solution is then cooled to crystallize out the optically active enantiomer. Optically active p-hydroxyphenylglycine benzenesulfonate, optically active p-hydroxyphenylglycine p-ethylbenzenesulfonate, optically active p-hydroxyphenylglycine o-toluenesulfonate or optically active p-hydroxyphenylglycine sulfosalicylate is thereby obtained.

17 Claims, No Drawings

PROCESS FOR THE OPTICAL RESOLUTION OF DL-P-HYDROXY-PHENYLGLYCINE

This is a Rule 60 Continuation Application of Ser. No. 756,079 filed on Jan. 3rd, 1977, now abandoned and which claims the priority of Japanese patent application No. 3344/1976 filed on Jan. 13th, 1976 and Japanese patent application No. 3345/1976 filed on Jan. 13th, 1976.

This invention relates to a process for the optical resolution of DL-p-hydroxyphenylglycine.

D-p-hydroxyphenylglycine is useful as a starting material in the synthesis of semi-synthetic penicillins or cephalosporins.

Known methods of resolving DL-p-hydroxyphenylglycine may be divided into three groups; i.e., biochemical method, chemical method and physicochemical method. According to the biochemical resolution method, D-p-hydroxyphenylglycine is prepared by assymmetric oxidation of DL-p-hydroxyphenylglycine with microorganisms belonging to the genus Fusarium, followed by separating the D-enantiomer from its reaction mixture (Japanese patent application No. 90554/1973). On the other hand, the chemical method comprises converting DL-p-hydroxyphenylglycine into N-benzyloxycarbonyl, N-chloroacetyl or an N-benzyl derivative thereof, reacting said N-acyl derivative with quinine, dihydroabiethylamine and so forth, allowing the resultant diastereoisomers to crystallize out fractionally, and then liberating optically active p-hydroxyphenylglycine therefrom [J. Chem. Soc. (C), 1971, 1920–1922; Japanese patent application Nos. 90591/1973 and 118542/1973]. Further, the physicochemical resolution method is carried out by preferential crystallization of DL-p-hydroxyphenylglycine p-toluenesulfonate or DL-p-hydroxyphenylglycine m-xylenesulfonate into each of its optically active enantiomers (Japanese patent application Nos. 11423/1974 and 50993/1974). Among these known methods, the biochemical method is still not advantageous in that it requires some complicated procedures as, for example, the fermentation of microorganisms prior to the assymmetric oxidation and it is difficult to separate the D-enantiomer from the reaction mixture. The chemical resolution method mentioned above requires the use of expensive resolving agents. Moreover, in said chemical method, it is difficult to remove the acyl groups (i.e., benzyloxycarbonyl, chloroacetyl and benzyl) from the optically active N-acyl-p-hydroxyphenylglycine without racemization of p-hydroxyphenylglycine.

Generally; a racemic modification of an organic compound can be resolved by preferential crystallization into each of its optically active enantiomers if the modification exists substantially in the form of the racemic mixture. However, it is impossible to predict what kind of racemic modification has such beneficial properties. It is likewise impossible to predict whether resolution of a given racemic modification is possible. Therefore, each pair of optically active enantiomers must be further studied experimentally to determine whether preferential crystallization can be accomplished. It is advantageous to commercially produce an optically active enantiomer by the preferential crystallization method. However, DL-p-hydroxyphenylglycine itself can not be resolved by the preferenetial crystallization method.

As a result of various investigations it has now been found that the salts of p-hydroxyphenylglycine with benzenesulfonic acid, p-ethylbenzenesulfonic acid, o-toluenesulfonic acid or sulfosalicylic acid have many beneficial properties which make them suitable for preferentially crystallizing them out into each of their optically active enantiomers. These properties are as follows: The racemic modification of each one of p-hydroxyphenylglycine benzenesulfonate, p-hydroxyphenyglycine p-ethylbenzenesulfonate, p-hydroxyphenylglycine o-toluenesulfonate and p-hydroxyphenylglycine sulfosalicylate is more soluble than the corresponding enantiomers thereof. A saturated solution of the racemic modification does not dissolve any more of the individual enantiomer. The supersaturated solution of an enantiomer of these salts is stable during the preferential crystallization. Additionally, prompt crystallization of the seeded enantiomer is afforded.

One object of the present invention is to provide a novel and useful process for resolving DL-p-hydroxyphenylglycine. Another object of the invention is to provide a process for resolving DL-p-hydroxyphenylglycine in a high yield and in a simple and convenient manner. Still another object of the invention is to provide an economical and commercially useful process for preparing optically active p-hydroxyphenylglycine. A further object of the invention is to provide novel intermediates which are useful in preparing optically active p-hydroxyphenylglycine. Still further objects of the invention will be apparent from the description which follows.

According to the present invention, optically active p-hydroxyphenylglycine benzenesulfonate, p-hydroxyphenylglycine p-ethylbenzenesulfonate, p-hydroxyphenylglycine o-toluenesulfonate or p-hydroxyphenylglycine sulfosalicylate can be prepared by the steps of producing a supersaturated solution of DL-p-hydroxyphenylglycine benzenesulfonate, DL-p-hydroxyphenylglycine p-ethylbenzenesulfonate, DL-p-hydroxyphenylglycine o-toluenesulfonate or DL-p-hydroxyphenylglycine sulfosalicylate in a solvent; seeding or dissolving one of the optically active enantiomers thereof into the supersaturated solution thus making it the predominant enantiomer to crystallize out preferentially; and then recovering it from the solution. p-hydroxyphenylglycine benzenesulfonate, p-hydroxyphenylglycine p-ethylbenzenesulfonate, p-hydroxyphenylglycine o-toluenesulfonate and p-hydroxyphenylglycine sulfosalicylate, in the form of either the racemic modification or optically active enantiomer, are novel compounds and can be readily prepared. For example, DL-p-hydroxyphenylglycine benzenesulfonate, DL-p-hydroxyphenylglycine p-ethylbenzenesulfonate, DL-p-hydroxyphenylglycine o-toluenesulfonate and DL-p-hydroxyphenylglycine sulfosalicylate can be prepared by neutralizing DL-p-hydroxyphenylglycine with benzenesulfonic acid, p-ethylbenzenesulfonic acid, o-toluenesulfonic acid or sulfosalicylic acid in a suitable solvent (e.g., water). Optically active enantiomers of p-hydroxyphenylglycine benzenesulfonate, p-hydroxyphenylglycine p-ethylbenzenesulfonate, p-hydroxyphenylglycine o-toluenesulfonate and p-hydroxyphenylglycine sulfosalicylate are also prepared in the same manner as above.

The supersaturated solution of the racemic modification can be prepared by applying conventional procedures such as refrigeration, concentration, addition of an appropriate solvent or a combination of these operations to a solution of DL-p-hydroxyphenylglycine benzenesulfonate, DL-p-hydroxyphenylglycine p-ethylbenzenesulfonate, DL-p-hydroxyphenylglycine o-toluenesulfonate or DL-p-hydroxyphenylglycine sulfosalicylate. However, it is most convenient to prepare by cooling a hot solution saturated with DL-p-hydroxyphenylglycine benzenesulfonate, DL-p-hydroxyphenylglycine p-ethylbenzenesulfonate, DL-p-hydroxyphenylglycine o-toluenesulfonate or DL-p-hydroxyphenylglycine sulfosalicylate, because the solubility thereof increases with the increase in temperature. Additionally, DL-p-hydroxyphenylglycine benzenesulfonate, DL-p-hydroxyphenylglycine p-ethylbenzenesulfonate, DL-p-hydroxyphenylglycine o-toluenesulfonate and DL-p-hydroxyphenylglycine sulfosalicylate, which are employed in preparing the supersaturated solution, may not always be an equal mixture of the D- and L-enantiomers. It is convenient to use an unequal mixture thereof as the starting material of the present invention, because the predominant enantiomer in the mixture may, upon cooling, be spontaneously crystallized out from the supersaturated solution of said compound.

When the supersaturated solution of the racemic modification is prepared as above, a small amount of crystals of one of the enantiomers is added to the supersaturated solution as a seed, and the mixture is stirred. Preferential crystallization of the enantiomer, corresponding to the one seeded, takes place. Alternatively, a small amount of one of the enantiomers is dissolved in a hot solution of the racemic modification in order to make said enantiomer predominant over the other enantiomer in the solution. The solution is then cooled, whereby spontaneous crystallization of the predominant enantiomer takes place. It is also possible to combine these procedures. That is, a part of the crystals of one of the enantiomers is dissolved in the solution of the racemic modification and the remaining part of the seed crystals is used to seed the supersaturated solution in which one of the enantiomers is dominant over the other. In this case, the amount of seed added can be minimized. The seed crystals employed in the present invention should have a high optical purity. The greater the amount of the seed, the better the resultant resolution. However, the practical proportion of the added seed is generally within the range of about 0.01 to 5% based on the weight of the solution. Although the temperature at which the preferential crystallization is carried out is not critical for the invention, a temperature of 5° to 80° C. is preferred. The crystallization is enhanced by stirring the solution. Further, when DL-p-hydroxyphenylglycine benzenesulfonate or DL-p-hydroxyphenylglycine p-ethylbenzenesulfonate is employed as the p-hydroxyphenylglycine salt of the invention, it is preferred to carry out the preferential crystallization in the presence of benzenesulfonic acid or p-ethylbenzenesulfonic acid. Any inert solvent in which DL-p-hydroxyphenylglycine benzenesulfonate, DL-p-hydroxyphenylglycine p-ethylbenzenesulfonate, DL-p-hydroxyphenylglycine o-toluenesulfonate or DL-p-hydroxyphenylglycine sulfosalicylate can be dissolved and which can afford prompt crystallization of the compound is suitable for the purpose of preferential crystallization. Examples of inert solvents suitable for this process are water, an alkanol having one to six carbon atoms (e.g., methanol, ethanol, butanol), an alkanone having three to six carbon atoms (e.g., acetone) and a mixture of water and said alkanol or alaknone. However, water is the most suitable solvent from an industrial standpoint.

The mother liquor which is obtained after isolation of one of the enantiomers by the above-mentioned procedure can be again employed for the optical resolution of the other enantiomer. For example, when a certain amount of the racemic modification which is equal to the amount of the enantiomer previously separated, is added to the mother liquor, the same conditions as the previous operation can be obtained except that the predominant enantiomer in the solution will be the antipode of the enantiomer previously separated. Thus, the operation of preferential crystallization can be repeated indefinitely, and the racemic modification which is supplied can be successfully and entirely resolved into each of the D- and L-enantiomers.

The process of the present invention can be carried out batchwise, as mentioned above, or in a continuous manner. A continuous process, for example, would comprise passing the supersaturated solution through a column containing the seed crystals, and allowing an optically active p-hydroxyphenylglycine benzenesulfonate, p-hydroxyphenylglycine p-ethylbenzenesulfonate, p-hydroxyphenylglycine o-toluenesulfonate or p-hydroxyphenylglycine sulfosalicylate to crystallize out in the column. Alternatively, the process of the present invention can be carried out by immersing seeding plates of optically active enantiomers in the supersaturated solution and allowing the optically active enantiomers to crystallize out on the seeding plates.

Depending on the degree of supersaturation and the amount of crystallization, the crystals of the optically active enantiomers thus obtained may sometimes be optically impure. The crude crystals, however, can be easily purified because the solubility of the racemic modification is sufficiently higher than that of each enantiomer and the one optically active enantiomer can not remain dissolved in the saturated solution of the racemic modification. For example, optically pure crystals of p-hydroxyphenylglycine benzenesulfonate, p-hydroxyphenylglycine p-ethylbenzenesulfonate, p-hydroxyphenylglycine o-toluenesulfonate and p-hydroxyphenylglycine sulfosalicylate can be obtained by adding the crude crystals to sufficient solvent to produce a solution saturated or almost saturated with respect to the racemic modification in the crude crystals, stirring the solution, and recovering the resultant crystals from the solution. Alternatively, the optically pure crystals of p-hydroxyphenylglycine benzenesulfonate, p-hydroxyphenylglycine p-ethylbenzenesulfonate, p-hydroxyphenylglycine o-toluenesulfonate and p-hydroxyphenylglycine sulfosalicylate can be obtained by dissolving the crude crystals at an elevated temperature in a small amount of a solvent which will dissolve the racemic modification in the crude crystals, saturating or almost saturating the solution with respect to the racemic modification to crystallize out the enantiomer, and recovering the crystallized enantiomer from the solution. Such operations as refrigeration, concentration, addition of a solvent or combination thereof may be used for saturating or almost saturating the solution. The same solvent as described above can also be employed for this purpose. In order to promote crystallization of the optically active enantiomer, crystals of the optically active enantiomer may be added as a seed to the solution saturated or almost saturated with the racemic modification. When only a small amount of solvent is needed due to the low content of the racemic modification in the crude crystals or the high solubility of the racemic modification, it is convenient to carry out the operation by adding a suitable amount of a solution saturated with the racemic modification.

According to the present invention, the optically active enantiomer thus obtained can be readily converted into optically active p-hydroxyphenylglycine. Optically active p-hydroxyphenylglycine is prepared by treating optically active p-hydroxyphenylglycine benzenesulfonate, p-hydroxyphenylglycine p-ethylbenzenesulfonate, p-hyroxyphenylglycine o-toluenesulfonate or p-hydroxyphenylglycine sulfosalicylate with an alkaline agent such as an inorganic base (e.g., sodium hydroxide, potassium hydroxide, lithium hydroxide, ammonium hydroxide), an organic base (e.g., methylamine, ethylamine, cyclohexylamine) or an ion exchange resin (e.g., Amberlite IR-120, Dowex 50W) to remove benzenesulfonic acid, p-ethylbenzenesulfonic acid, o-toluenesulfonic acid or sulfosalicylic acid therefrom. Benzenesulfonic acid, p-ethylbenzenesulfonic acid, o-toluenesulfonic acid and sulfosalicyclic acid thus recovered can be re-used for preparing the starting materials of the invention, i.e., the corresponding salts of DL-p-hydroxyphenylglycine.

Practical and presently-preferred embodiments of the present invention are illustratively shown in the following Examples.

EXAMPLE 1

50 g of DL-, D- or L-p-hydroxyphenylglycine and 110.8 g of benzenesulfonic acid 3/2 hydrate are dissolved in 280 ml of water under heating, and the solution is treated with 5 g of activated charcoal. Then, the solution is stirred under ice-cooling. Crystalline precipitates are collected by filtration, washed with water and dried. 70.1 g of DL-, D- or L-p-hydroxyphenylglycine benzenesulfonate are obtained as crystals. The filtrate obtained in the above-mentioned procedure is concentrated to about half the volume thereof and crystalline precipitates are again collected in the same manner as described above. 13.2 g of DL-, D- or L-p-hydroxyphenylglycine benzenesulfonate are further recovered. Over-all yield: 85.2%

The physico-chemical properties of the salts thus obtained are shown in Table 1.

TABLE 1

| p-hydroxyphenyl-glycine benzene-sulfonate | Melting point (°C.) | Specific rotation $[\alpha]_D^{25}$ (C=1, H$_2$O) | Solubility (g/100 ml of solvent*) Temperature | | |
|---|---|---|---|---|---|
| | | | 20° C. | 30° C. | 40° C. |
| DL-modification | 221–223 | ±0.0 | 15.4 | 24.1 | 35.0 |
| D-enantiomer | 227–230 | −67.3 | 7.7 | 11.0 | 16.7 |
| L-enantiomer | 227–230 | +67.3 | 7.7 | 11.0 | 16.7 |

Note:
*an aqueous 0.5 M benzenesulfonic acid solution

EXAMPLE 2

40 g of DL-, D- or L-p-hydroxyphenylglycine and 97.8 g of p-ethylbenzenesulfonic acid are dissolved in 240 ml of water under heating, and the solution is treated with 3 g of activated charcoal. Then, the solution is treated in the same manner as described in Example 1. 68.6 g of DL-, D- or L-p-hydroxyphenylglycine p-ethylbenzenesulfonate are obtained. Over-all yield: 81.1%

The physico-chemical properties of the salts thus obtained are shown in Table 2.

TABLE 2

| p-hydroxyphenyl-glycine p-ethyl-benzenesulfonate | Melting point (°C.) | Specific rotation $[\alpha]_D^{25}$ (C=1, H$_2$O) | Solubility (g/100 ml of solvent*) Temperature | | |
|---|---|---|---|---|---|
| | | | 20° C. | 30° C. | 40° C. |
| DL-modification | 192–194 | ±0.0 | 19.3 | 33.2 | 52.1 |
| D-enantiomer | 209–211 | −62.7 | 10.3 | 14.2 | 21.8 |
| L-enantiomer | 209–211 | +62.7 | 10.3 | 14.2 | 21.8 |

Note:
*an aqueous 3 M p-ethylbenzenesulfonate acid solution

EXAMPLE 3

200 g of DL-, D- or L-p-hydroxyphenylglycine and 262 g of o-toluenesulfonic acid dihydrate are dissolved in 800 ml of water under heating, and the solution is treated with 5 g of activated charcoal. Then, the solution is treated in the same manner as described in Example 1. 394 g of DL-, D- or L-p-hydroxyphenylglycine o-toluenesulfonate are obtained. Over-all yield: 97.1%

The physico-chemical properties of the salts thus obtained as shown in Table 3.

TABLE 3

| p-hydroxyphenyl-glycine o-toluenesulfonate | Melting point (°C.) | Specific rotation $[\alpha]_D^{25}$ (C=1, H$_2$O) | Solubility (g/100 ml of water) Temperature | | |
|---|---|---|---|---|---|
| | | | 20° C. | 30° C. | 40° C. |
| DL-modification | 213–216 | ±0.0 | 12.3 | 16.0 | 21.0 |
| D-enantiomer | 221–224 | −66.6 | 7.7 | 9.6 | 12.2 |
| L-enantiomer | 221–224 | +66.6 | 7.7 | 9.6 | 12.2 |

EXAMPLE 4

DL-, D- or L-p-hydroxyphenylglycine sulfosalicylate is prepared in the same manner as described in Example 1. The physico-chemical properties of said salts are shown in Table 4.

TABLE 4

| p-hydroxyphenyl-glycine sulfo-salicylate mono-hydrate | Melting point (°C.) | Specific rotation $[\alpha]_D^{25}$ (C=1, H$_2$O) | Solubility (g/100 ml of water) Temperature | |
|---|---|---|---|---|
| | | | 20° C. | 30° C. |
| DL-modification | 221–223 | ±0.0 | 18.2 | 26.3 |
| D-enantiomer | 223–225 | −56.6 | 10.0 | 14.0 |
| L-enantiomer | 223–225 | +56.6 | 10.0 | 14.0 |

EXAMPLE 5

29.6 g of DL-p-hydroxyphenylglycine benzenesulfonate and 2.8 g of D-p-hydroxyphenylglycine benzenesulfonate are dissolved in 100 ml of an aqueous 0.5 M benzenesulfonic acid solution under heating. After the solution is cooled to 25° C., 0.1 g of D-p-hydroxyphenylglycine benzenesulfonate is seeded thereto, and the mixture is stirred at the same temperature for 55 minutes. Crystalline precipitates are collected by filtration, washed with a small amount of cold water and then dried. 7.4 g of D-p-hydroxyphenylglycine benzenesulfonate are obtained.

$[\alpha]_D^{25}$ −63.9° (C=1, H$_2$O)

Optical purity: 95.0%

EXAMPLE 6

7.6 g of DL-p-hydroxyphenylglycine benzenesulfonate and a small amount of an aqueous 0.5 M benzenesulfonic acid solution are added to the mother liquor obtained in Example 5, and said mother liquor is heated until dissolution is complete. The resultant solution is cooled to 25° C. Then, 0.1 g of L-p-hydroxyphenylglycine benzenesulfonate is added as a seed to the solution, and the mixture is stirred for 50 minutes. Crystalline precipitates are collected by filtration, washed with a small amount of cold water and then dried. 8.4 g of L-p-hydroxyphenylglycine benzenesulfonate are obtained.

$[\alpha]_D^{25}$ +63.3° (C=1, H$_2$O)
Optical purity: 94.1%

EXAMPLE 7

24.2 g of DL-p-hydroxyphenylglycine benzenesulfonate are dissolved in 100 ml of an aqueous 0.5 M benzenesulfonic acid solution under heating. After the solution is cooled to 22° C., 0.05 g of D-p-hydroxyphenylglycine benzenesulfonate is added as a seed thereto, and the mixture is stirred at the same temperature for 35 minutes. Crystalline precipitates are collected by filtration, washed with cold water and then dried in vacuo at room temperature. 0.53 g of D-p-hydroxyphenylglycine benzenesulfonate is obtained.

$[\alpha]_D^{25}$ −61.5° (C=1, H$_2$O)
Optical purity: 91.4%

EXAMPLE 8

32.0 g of DL-p-hydroxyphenylglycine p-ethylbenzenesulfonate are dissolved in 100 ml of an aqueous 3 M p-ethylbenzenesulfonic acid solution under heating. After the solution is cooled to 25° C., 0.4 g of D-p-hyroxyphenylglycine p-ethylbenzenesulfonate is added as a seed thereto, and the mixture is stirred at the same temperature for 55 minutes. Crystalline precipitates are collected by filtration, washed with a small amount of cold water and then dried. 2.4 g of D-p-hydroxyphenylglycine p-ethylbenzenesulfonate are obtained.

$[\alpha]_D^{25}$ −60.2° (C=1, H$_2$O)
Optical purity: 96%

EXAMPLE 9

2.2 g of DL-p-hyroxyphenylglycine p-ethylbenzenesulfonate and a small amount of an aqueous 3 M p-ethylbenzenesulfonic acid solution are added to the mother liquor obtained in Example 8, and said mother liquor is heated until dissolution is complete. The resultant solution is cooled to 25° C. Then, 0.29 g of L-p-hydroxyphenylglycine p-ethylbenzenesulfonate is added as a seed to the solution, and the mixture is stirred for 45 minutes. Crystalline precipitates are collected by filtration, washed with a small amount of cold water and then dried. 4.8 g of L-p-hyroxyphenylglycine p-ethylbenzenesulfonate are obtained.

$[\alpha]_D^{25}$ +59.8° (C=1, H$_2$O)
Optical purity: 95.4%

EXAMPLE 10

39.0 g of DL-p-hydroxyphenylglycine, p-ethylbenzenesulfonate are dissolved in 100 ml of an aqueous 0.5 M p-ethylbenzenesulfonic acid solution under heating. After the solution is cooled to 13° C., 0.25 g of D-p-hydroxyphenylglycine p-ethylbenzenesulfonate is added as a seed thereto, and the mixture is stirred at the same temperature for 30 minutes. Crystalline precipitates are collected by filtration. 2.3 g of D-p-hydroxyphenylglycine p-ethylbenzenesulfonate are obtained.

$[\alpha]_D^{25}$ −53.0° (C=1, H$_2$O)
Optical purity: 84.5%

EXAMPLE 11

210 g of DL-p-hydroxyphenylglycine o-toluenesulfonate and 20.9 g of D-p-hydroxyphenylglycine o-toluenesulfonate are dissolved in 600 ml of water under heating. After the solution is cooled to 45° C., 0.5 g of D-p-hyroxyphenylglycine o-toluenesulfonate is added as a seed thereto, and the mixture is stirred at the same temperature for 60 minutes. Crystalline precipitates are collected by filtration, whereby D-p-hydroxyphenylglycine o-toluenesulfonate is obtained as crystals.

DL-p-hydroxyphenyglycine o-toluenesulfonate and water are added to the mother liquor obtained above in order that the same conditions as the previous operation can be obtained except that the predominant enantiomer in the solution is the antipode of the enantiomer previously separated. After dissolving the added salt to the mother liquor under heating, 0.5 g of L-p-hydroxyphenylglycine o-toluenesulfonate is added as a seed thereto, and the mixture is stirred for 80 minutes. Crystalline precipitates are collected by filtration, whereby L-p-hydroxyphenylglycine o-toluenesulfonate is obtained as crystals.

The above-mentioned operations are further repeated three times, whereby D- and L-p-hydroxyphenylglycine o-toluenesulfonate is obtained alternatively as shown in the following Table 5.

TABLE 5

| Number of operations repeated | Components of the solution | | | Operation time (minutes) | Yield | Optical purity |
| --- | --- | --- | --- | --- | --- | --- |
| | A* | B** | C*** | | | |
| 1 | 210 g | 20.9 g (D-isomer) | 600 ml | 60 | 46.6 g (D-isomer) | 95.3% |
| 2 | 210 g | 23.5 g (L-isomer) | 600 ml | 80 | 50.6 g (L-isomer) | 95.9% |
| 3 | 210 g | 24.5 g (D-isomer) | 600 ml | 70 | 54.3 g (D-isomer) | 97.2% |
| 4 | 210 g | 27.8 g (L-isomer) | 600 ml | 70 | 55.4 g (L-isomer) | 95.1% |
| 5 | 210 g | 24.4 g (D-isomer) | 600 ml | 50 | 55.8 g (D-isomer) | 96.5% |

Note:
*DL-modification
**Optically active enantiomer
***water

EXAMPLE 12

24.5 g of DL-p-hydroxyphenylglycine o-toluenesulfonate and 3.0 g of L-p-hydroxyphenylglycine o-toluenesulfonate are dissolved in 100 ml of water under heating. After the solution is cooled to 30° C., 0.1 g of L-p-hydroxyphenylglycine o-toluenesulfonate is seeded thereto, and the mixture is stirred at the same temperature for 90 minutes. Crystalline precipitates are collected by filtration. 6.9 g of L-p-hydroxyphenylglycine o-toluenesulfonate are obtained.

$[\alpha]_D^{25}$ +65.3° (C=1, H$_2$O)
Optical purity: 98.1%

EXAMPLE 13

7.0 g of DL-p-hyroxyphenylglycine o-toluenesulfonate are added to the mother liquor obtained in Example 12, and said mother liquor is heated until dissolution is complete. The resultant solution is cooled to 30° C. Then, 0.1 g of D-p-hdyroxyphenylglycine o-toluenesulfonate is added as a seed to the solution, and the mixture is treated in the same manner as described in Example 12. 7.3 g of D-p-hydroxyphenylglycine o-toluenesulfonate are obtained.

$[\alpha]_D^{25}$ −65.5° (C=1, H₂O)

Optical purity: 98.4%

EXAMPLE 14

76.5 g of DL-p-hydroxyphenylglycine sulfosalicylate and 1.8 g of D-p-hyroxyphenylglycine sulfosalicylate are dissolved in 300 ml of water under heating. After the solution is cooled to 25° C., 0.3 g of D-p-hydroxyphenylglycine sulfosalicylate is added as a seed thereto, and the mixture is stirred at the same temperature for 120 minutes. Crystalline precipitates are collected by filtration, washed with a small amount of cold water and dried in vacuo at room temperature. 4.9 g of D-p-hyroxyphenylglycine sulfosalicylate are obtained.

$[\alpha]_D^{25}$ −41.4° (C=1, H₂O)

Optical purity: 73.1%

4.5 g of D-p-hydroxyphenylglycine sulfosalicylate thus obtained as dissolved in 8 ml of water under heating. The solution is stirred at 25° C. for 3 hours. Then, crystalline precipitates are collected by filtration and dried. 2.6 g of optically pure crystals of D-p-hydroxyphenylglycine sulfosalicylate are obtained.

$[\alpha]_D^{25}$ −56.6° (C=1, H₂O)

2.5 g of D-p-hydroxyphenylglycine sulfosalicylate are dissolved in 30 ml of water. The solution is passed through a column of 10 ml of Amberlite IR-120. After the column is washed with water, said column is eluted with aqueous ammonia. Then, the eluate thus obtained is concentrated to dryness. 1.1 g of D-p-hyroxyphenylglycine are obtained. M.p. 224°–225° C. (decomp.)

$[\alpha]_D^{25}$ −159.0° (C=1, N—HCl)

Analysis calculated for C₈H₉O₃N: C, 57.48; H, 5.43; M, 8.38. Found C, 55.83; H, 5.36; N, 8.29.

EXAMPLE 15

4.9 g of DL-p-hydroxyphenylglycine sulfosalicylate are added to the mother liquor obtained in Example 14, and said mother liquor is heated until dissolution is complete. The resultant solution is cooled to 25° C. Then, 0.3 g of L-p-hydroxyphenylglycine sulfosalicylate is added as a seed to the solution, and the mixture is treated in the same manner as described in Example 14. 5.4 g of L-p-hydroxyphenylglycine sulfosalicylate are obtained.

$[\alpha]_D^{25}$ +45.8° (C=1, H₂O)

Optical purity: 81%

What we claim is:

1. A process for resolving a racemic modification selected from the group consisting of DL-p-hydroxyphenylglycine benzenesulfonate , DL-p-hydroxyphenylglycine p-ethylbenzenesulfonate, DL-p-hyroxyphenylglycine o-toluenesulfonate and DL-p-hyroxyphenylglycine sulfosalicylate which comprises preparing a supersaturated solution of said racemic modification in an inert solvent therefore, adding crystals of a desired enantiomer of said modification to the solution before and/or after said solution reaches the condition of supersaturation so that the proportion of one of the enantiomers becomes greater than that of the other enantiomer, allowing crystallization to take place, and recovering the separated crystals therefrom.

2. The process of claim 1 in which said racemic modification is DL-p-hyroxyphenylglycine benzenesulfonate, DL-p-hydroxyphenylglycine p-ethylbenzenesulfonate or DL-p-hydroxyphenylglycine o-toluenesulfonate.

3. The process of claim 1 in which said racemic modification is DL-p-hyroxyphenylglycine o-toluenesulfonate.

4. The process of claim 1 in which said inert solvent is water, an alkanol of one to six carbon atoms, an alkanone of three to six carbon atoms or a mixture of water and said alkanol or alkanone.

5. The process of claim 2 in which said inert solvent is water, an alkanol of one to six carbon atoms, an alkanone of three to six carbon atoms or a mixture of water and said alkanol or alkanone.

6. The process of claim 3 in which said inert solvent is water, an alkanol of one to six carbon atoms, an alkanone of three to six carbon atoms or a mixture of water and said alkanol or alkanone.

7. The process of claim 1 in which the desired enantiomer is inoculated as seed crystals to the supersaturated solution of the racemic modification.

8. The process of claim 2 in which the desired enantiomer is inoculated as seed crystals to the supersaturated solution of the racemic modification.

9. The process of claim 3 in which the desired enantiomer is inoculated as seed crystals to the supersaturated solution of the racemic modification.

10. The process of claim 1 in which the desired enantiomer is dissolved in a solution of the racemic modification and the solution is cooled to produce a supersaturated solution.

11. The process of claim 2 in which the desired enantiomer is dissolved in a solution of the racemic modification and the solution is cooled to produce a supersaturated solution.

12. The process of claim 3 in which the desired enantiomer is dissolved in a solution of the racemic modification and the solution is cooled to produce a supersaturated solution.

13. The process of claim 1 in which the desired enantiomer is dissolved in a solution of the racemic modification, and the solution is allowed to cool and is inoculated with the desired enantiomer as seed crystals.

14. The process of claim 2 in which the desired enantiomer is dissolved in a solution of the racemic modification, and the solution is allowed to cool and is inoculated with the desired enantiomer as seed crystals.

15. The process of claim 3 in which the desired enantiomer is dissolved in a solution of the racemic modification, and the solution is allowed to cool and is inoculated with the desired enantiomer as seed crystals.

16. The process of claim 1 in which additional racemic modification is dissolved in the mother liquor obtained after the recovery of the desired enantiomer, at an elevated temperature thus producing another supersaturated solution, a small amount of the other enantiomer are allowed to separate out and recovered.

17. The process of claim 16 wherein said process is repeated a plurality of times whereby said optically active enantiomers are successively and alternatively separated from said racemic modification.

* * * * *